United States Patent [19]

Doellein

[11] Patent Number: 5,518,536
[45] Date of Patent: May 21, 1996

[54] ALKALINE EARTH METAL-HEPTANE DIONATE COMPOUNDS

[75] Inventor: Guenther Doellein, Hannover, Germany

[73] Assignee: Solvay Barium Strontium GmbH, Hannover, Germany

[21] Appl. No.: 490,997

[22] Filed: Jun. 15, 1995

Related U.S. Application Data

[62] Division of Ser. No. 158,374, Jan. 29, 1993, Pat. No. 5,451,434, which is a continuation of Ser. No. 847,266, Mar. 10, 1992, abandoned.

[30] Foreign Application Priority Data

Mar. 18, 1991 [DE] Germany ............................ 41 08 731.8

[51] Int. Cl.$^6$ ............................................. C23C 16/18
[52] U.S. Cl. ......................... 106/1.25; 106/1.26; 568/412
[58] Field of Search .................................. 106/1.25, 1.26; 568/412

[56] References Cited

U.S. PATENT DOCUMENTS

| | | | |
|---|---|---|---|
| 3,098,863 | 7/1963 | Dessauer et al. | 260/439 |
| 3,946,057 | 3/1976 | Reedy | 556/40 |
| 4,127,361 | 11/1978 | Hellier et al. | 427/255.6 |
| 4,251,233 | 2/1981 | Seivers et al. | 44/68 |
| 4,915,988 | 4/1990 | Erbil | 427/252 |
| 4,970,093 | 11/1990 | Sievers et al. | 427/38 |
| 5,028,724 | 7/1991 | Ivankovits et al. | 556/40 |
| 5,139,999 | 8/1992 | Gordon et al. | 505/1 |
| 5,140,003 | 8/1992 | Mueller | 505/1 |
| 5,225,561 | 7/1993 | Kirlin et al. | 546/256 |
| 5,280,012 | 1/1994 | Kirlin et al. | 505/1 |
| 5,346,730 | 9/1994 | Kruck et al. | 427/584 |
| 5,451,434 | 9/1995 | Doellein | 427/255.2 |
| 5,453,494 | 9/1995 | Kirlin et al. | 505/100 |

FOREIGN PATENT DOCUMENTS

| | | |
|---|---|---|
| 55459 | 7/1982 | European Pat. Off. |
| 297348 | 1/1989 | Germany. |
| 4124686 | 1/1992 | Germany. |
| 4122449 | 1/1992 | Germany. |

OTHER PUBLICATIONS

Chemical Abstracts 116(6):50311m, 1992 (no month available).
Chemical Abstracts 114(26):258508x, 1991 (no month available).
Berg et al., "Fractional Sublimation of Various Metal Chelates of Dipivaloylmethane", *Analytica Chimica Acta*, vol. 60, pp. 117–125.
Dickinson et al., "Chemical Vapor Deposition of $YBa_2Cu_3O_{7-x}$ Superconducting Films", *J. Appl. Phys.*, vol. 66, No. 1, pp. 444–447 (1989).
Hammond et al., "Chelates of β–Diketones. V. Preparation and Properties of Chelates Containing Sterically Hindered Ligands", *Inorganic Chemistry*, vol. 2, No. 1, pp. 73–76.
Murdock et al., "Acylation of Metal Chelates. Part I.", pp. 2153–2162 (1962).

*Primary Examiner*—Helene Klemanski
*Attorney, Agent, or Firm*—Evenson, McKeown, Edwards & Lenahan

[57] ABSTRACT

Alkaline earth metal heptane dionates which have uniform evaporation properties in a vacuum and are therefore highly suitable for use in CVD synthesis for depositing layers containing alkaline earth metal useful in fields such as the production of high temperature superconductors.

8 Claims, 5 Drawing Sheets

ALKALINE EARTH METAL-HEPTANE DIONATE COMPOUNDS

This application is a division of application Ser. No. 08/158,374, filed Nov. 29, 1994, now U.S. Pat. No. 5,451,434 which in turn is a continuation of application Ser. No. 07/847,266, filed Mar. 10, 1992, now abandoned.

BACKGROUND OF THE INVENTION

This invention relates to novel alkaline earth metal-heptane dionate compounds, to a process for preparing such compounds, and to a process for using such compounds to deposit layers containing alkaline earth metal.

Alkaline earth metal-heptane dionate compounds of the general formula (I), $M(R)_2$, wherein M is calcium, strontium or barium, and R is 2,6-dimethyl-3,5-heptane dionate, 2,2,6-trimethyl-3,5-heptane dionate or 2,2,6,6-tetramethyl-3,5-heptane dionate, are already known from the scientific literature.

It is also already known that these compounds are vaporizable and can therefore be used for depositing layers containing alkaline earth metal, for instance in the production of superconductive, oxide-ceramic layers. However, the commercially available alkaline earth metal-heptane dionate compounds known in the art still have drawbacks. For instance, they have non-uniform weight loss or evaporation properties, so that the weight loss or evaporation rate soon drops from relatively high initial values to relatively low values.

SUMMARY OF THE INVENTION

It is the object of the invention to provide alkaline earth metal-heptane dionate compounds having advantageous properties.

A further object of the invention to provide alkaline earth metal-heptane dionate compounds which are particularly useful in metal organic chemical vapor deposition (MOCVD) methods.

Another object of the invention is to provide alkaline earth metal-heptane dionate compounds which exhibit more uniform weight loss or evaporation characteristics.

A still further object of the invention is to provide a process for preparing improved alkaline earth metal-heptane dionate compounds.

It is also an object of the invention to provide an improved process for depositing alkaline earth metal containing layers on substrates.

These and other objects of the invention are achieved by providing a vaporizable compound corresponding to the formula (I):

$$M(R)_2 \qquad (I)$$

wherein
M represents calcium, strontium or barium, and
R represents 2,6-dimethyl-3,5-heptane dionate, 2,2,6-trimethyl-3,5-heptane dionate, or 2,2,6,6-tetramethyl-3,5-heptane dionate;
the compound exhibiting a $^1$H-NMR spectrum free of a detectable water proton signal.

In accordance with a further preferred aspect of the invention, the objects are achieved by providing a process for preparing a compound corresponding to the Formula (I):

$$M(R)_2 \qquad (I)$$

wherein
M represents the metal calcium, strontium or barium, and
R represents 2,6-dimethyl-3,5-heptane dionate, 2,2,6-trimethyl-3,5-heptane dionate or 2,2,6,6-tetramethyl-3,5-heptane dionate,
the process comprising the steps of:
mixing a solution or suspension of a compound of the metal M in water or in a water-containing, water-miscible solvent with a diketone selected from the group consisting of 2,6-dimethyl-3,5-heptane dione, 2,2,6-trimethyl-3,5-heptane dione and 2,2,6,6-tetramethy-3,5-heptane dione to react the compound of the metal M with the diketone;
separating the resulting compound of Formula (I) from the mixture; and
vacuum drying the separated compound of Formula (I) at a temperature of at most 60° C. until the compound of Formula (I) exhibits a $^1$H-NMR spectrum in which a water proton signal cannot be detected.

According to yet another preferred aspect of the invention, the objects are achieved by providing a process for depositing an alkaline earth metal-containing layer on a substrate comprising decomposing in the presence of the substrate an alkaline earth metal-diketonate compound corresponding to the formula (I):

$$M(R)_2 \qquad (I)$$

wherein
M represents calcium, strontium or barium, and
R represents 2,6-dimethyl-3,5-heptane dionate, 2,2,6-trimethyl-3,5-heptane dionate or 2,2,6,6-tetramethyl-3,5-heptane dionate,
the alkaline earth metal-diketonate compound exhibiting a $^1$H-NMR spectrum in which a water proton signal cannot be detected.

BRIEF DESCRIPTION OF THE DRAWINGS

The invention will be described in further detail hereinafter with reference to the accompanying drawing figures in which.

DETAILED DESCRIPTION OF PREFERRED EMBODIMENTS

The invention relates to novel vaporizable compounds of the general formula (I):

$$M(R)_2 \qquad (I)$$

wherein M is calcium, strontium or barium, and R is 2,6-dimethyl-3,5-heptane dionate, 2,2,6-trimethyl-3,5-heptane dionate or 2,2,6,6-tetramethyl-3,5-heptane dionate, which are characterized in that a signal for water protons cannot be detected in the ¹H-NMR spectrum.

As used herein, the term "3,5-heptane dione" refers to compounds having the basic structure The term "3,5-heptane dionate" refers to compounds having the above basic structure from which one proton has been abstracted and which therefore have a negative charge.

Even at a high signal-to-noise ratio, for instance >600, a water signal cannot be identified. Of course, measurements must be made in an anhydrous solvent, in particular in deuterated solvents such as $D_6$-dimethyl sulfoxide.

The alkaline earth metal-heptane dionate compounds according to the invention differ from the compounds known in the prior art which are conventionally used in this technology in that no signal for water protons can be detected in the ¹H-NMR spectrum of a solution of the compounds according to the invention in a nonaqueous solvent, even when measuring in apparatus which operate according to the Fourier Transform (FT) principle and high spectra accumulation with a correspondingly high signal-to-noise ratio of the methyl protons.

Preferred compounds of the general formula (I) are those in which R is 2,2,6,6-tetramethyl-3,5-heptane dionate. Preferably M is barium. Particularly preferred compounds include calcium-, strontium- or barium-bis(2,2,6,6-tetramethyl-3,5-heptane dionate), especial barium-bis(2,2,6,6-tetramethyl-3,5-heptane dionate), which is called $Ba(TMHD)_2$ for short.

It is known that metal diketonates may exist in monomeric, oligomeric or polymeric form in the various aggregate states. The general formula (I) is intended to cover not only monomeric, but also oligomeric or polymeric forms of the compounds according to the invention.

A particularly advantageous property in which the compounds according to the invention differ from already known compounds of this type is their uniformweight loss or evaporation rate in a vacuum at elevated temperature.

If, for instance, a sample of the barium-bis(2,2,6,6-tetramethyl-3,5-heptane dionate), $Ba(TMHD)_2$, according to the invention is heated to a temperature of 200° C. at reduced pressure in a nitrogen atmosphere, and the percentage weight loss is determined, relative each time to the original weight of the sample used as 100% by weight, it will be noted that the ratio of the percentage weight loss within the first hour after the temperature of 200° C. has been reached and within the sixth hour after the temperature of 200° C. has been reached is about 1.5:1. If the measuring period after the temperature has been reached is divided into 6 periods of 1 hour each, the ratios of the percentage weight loss of one period compared with the following period is within a range of fluctuation of 0.7:1 to 1.5:1. The absolute value of the weight loss of the $Ba(TMHD)_2$ according to the invention over a period of at least 6 hours after a temperature of about 200° C. has been reached is about (3± 0.5) % by weight, relative to the total weight of the sample at the start of the test.

The weight loss, for instance, of the compounds according to the invention $Ca(TMHD)_2$ and $Sr(TMHD)_2$ is equally uniform. For example, if a sample of the $Ca(TMHD)_2$ according to the invention is heated to a temperature of 200° C. at reduced pressure in a nitrogen atmosphere and the percentage weight loss is determined, relative each time to the originally used weight of the sample as 100% by weight at the beginning of the test, it will be noted that the value of the percentage weight loss within the second hour after the temperature of 200° C. has been reached and the value of the weight losses within the sixth hour after the temperature of 200° C. has been reached have a ratio of about 0.6:1. If the measuring period after the temperature has been reached is divided into six periods of 1 hour each, the ratio of the percentage weight loss of the first period and the percentage weight loss of the second period is indeed 5.6:1. The ratios of the percentage weight loss of the second, third, fourth and fifth periods and the weight loss of the following period in each case lie within an advantageously low range of fluctuation of about 0.55:1 to 1.2:1. The absolute value of the weight loss of the $Ca(TMHD)_2$ according to the invention over a period of at least 5 hours after a temperature of about 200° C. has been reached is about (0.56±0.16) % by weight, relative to the total weight of the sample.

Such a uniform weight loss cannot be achieved with known heptane dionate compounds. With these compounds, rather, a very great percentage weight loss is observed within the first hour and a lower weight loss occurs from the second hour onwards after the heating temperature of 200° C. has been reached.

The evaporation rate of the compounds according to the invention is also advantageously constant over a long period. If, for instance, the evaporation rate of the compounds according to the invention, measured in mg/min, is determined at 220° C. in a vacuum over a period of 6 hours, it will be discovered that the evaporation rate after 6 hours is still about 69% of the original evaporation rate. In addition, the decrease is very uniform. Such a constant evaporation rate cannot be achieved with known alkaline earth metal-heptane dionates. With the known compounds, a much greater drop is observed and often also a change in the evaporation rate which is not constant. The evaporation rate for the known compounds of the prior art is usually especially large within the first two hours. An evaporation rate after 6 hours which amounts to 60% or more of the originally measured evaporation rate, is likewise a property in which the novel compounds differ from known compounds.

The invention also relates to a process for preparing a compound of the general formula (I) according to the invention. This process is characterized in that a solution or suspension of the compound of the metal M in water or in a water-containing solvent which is miscible with water is mixed with the diketone, the resulting product is separated and dried in a vacuum at a temperature of at most 60° C., until water protons can no longer be detected in the ¹H-NMR spectrum. In order to record a ¹H-NMR spectrum, the compound which is to be investigated is advantageously dissolved in an anhydrous solvent, in particular in a deuterated solvent such as $D_6$-DMSO.

Various inorganic or organic alkaline earth metal compounds may be used as starting compounds. Oxides and in particular hydroxides, for. instance calcium hydroxide, strontiumhydroxide, bariumhydroxide and also corresponding hydrates or calcium oxide, strontium oxide or barium oxide, are particularly suitable. To prepare compounds of the general formula (I) in which M is barium, it is particularly advantageous to start with barium hydroxide octahydrate. Obviously, one could also start with anhydrous barium hydroxide or bariumhydroxide monohydrate or other hydrates, and also from barium oxide.

Water or mixtures of water with water-miscible organic solvents are used as solvents. For instance, mixtures of water with short-chain aliphatic alcohols, for instance methanol or ethanol, may be used. It is particularly preferred to use water which contains no organic solvent. The molar ratio of alkaline earth metal compound to heptane dione compound is advantageously 1:2 to 1:2.05.

Advantageously, the heptane dione compound is added with intensive stirring to the solution or suspension of the alkaline earth metal compound.

If desired, the reaction mixture may be stirred further, for instance for up to 24 hours at elevated temperature, in order to complete the reaction. For the preparation of Ba(T-MHD)$_2$, a subsequent reaction phase with stirring of 8 to 12 hours at 40° to 50° C. temperature in the reaction mixture has proved advantageous.

The product may then be separated from the supernatant liquid phase at room temperature. Known methods are used for this purpose. Advantageously the product may be separated by filtration using a water-jet vacuum and a suction filter. Advantageously, the product is then subsequently washed with distilled water and substantially dried by suction. The subsequent drying is advantageously carried out at a very low pressure, e.g. <1 bar. The temperature during drying, which, as stated above, should be at most 60° C., is advantageously between 40° and 50° C.

The alkaline earth metal-heptane dionates of the general formula (I) obtainable according to the process of the invention may be used for all those fields of use in which such metal-heptane dionates are usually used. However, the compounds are particularly well suited for use in a process for depositing alkaline earth metal-containing layers.

It is already known to modify substrates by surface coating, for instance according to the MOCVD process, so that their surfaces have certain functional properties. For instance, layers such as conductive tracks, which conduct or semiconduct electric current, may be applied.

Thus, the invention also relates to a process for depositing layers containing alkaline earth metal using the compounds of the general formula (I) according to the invention.

The process according to the invention for depositing layers containing alkaline earth metal using alkaline earth metal-diketonate compounds is characterized in that a compound of the general formula (I):

$$M(R)_2 \qquad (I)$$

wherein M is calcium, strontium or barium, and R is 2,6-dimethyl-3,5-heptane dionate, 2,2,6-trimethyl-3,5-heptane dionate or 2,2,6,6-tetramethyl-3,5-heptane dionate and which exhibits a $^1$H-NMR spectrum in which water protons cannot be detected is used as the alkaline earth metal-diketonate compound.

As used herein, the term "alkaline earth metal" is intended to refer to calcium, strontium, barium or mixtures thereof, whereby the alkaline earth metals may be contained in the "zero" oxidation state (i.e. in metallic form) in the layers, or the alkaline earth metals may be present partially or also entirely in the form of in particular inorganic compounds, for instance as an oxide, a hydroxide, a carbonate or a nitride.

Preferably in such a process compounds are used in which R is 2,2,6,6-tetramethyl-3,5-heptane dionate. M is preferably barium. To deposit a barium-containing layer, it is especially preferred to use barium-bis(2,2,6,6-tetramethyl-3,5-heptane dionate).

A person skilled in the art may perform the deposition from the condensed phase or alternatively from the gas or vapor phase. It will be apparent to a person skilled in the art that, if desired, he may use not only a particular compound of the general formula (I), but also mixtures of such compounds in which M, R, or both vary.

In order to effect deposition from the condensed phase, the compound of Formula (I) is applied without solvent, or preferably dissolved in a solvent, to the substrate and the compound is then decomposed. Polar or non-polar, aprotic organic solvents, which may if desired have coordinating properties, may be used as the solvent. Suitable examples include aliphatic hydrocarbons such as pentane or petroleum spirits, aromatic hydrocarbons such as benzene or toluene, or ethers such as tetrahydrofuran. Furthermore, monobasic or polybasic, in particular aliphatic, alcohols, for instance methanol, ethanol, glycol or glycol derivatives, and also in particular aliphatic compounds having one, two or more primary, secondary or tertiary amino groups are also suitable. The compound is applied by immersing the substrate in the solution of the compound in known manner. The starting compound or a corresponding solution may also be sprayed, for instance, onto the substrate. In this way it is possible to coat even large surfaces very quickly.

Then the compound applied to the substrate is decomposed in order to deposit a layer containing alkaline earth metal, if desired at reduced pressure. Preferably, the compound is decomposed thermally. This may take place by introducing the substrate coated with the starting compound into an appropriately heated chamber, or by heating the substrate to the required temperature range before, during and/or after the application of the starting compound.

The thermal decomposition may also be radiation-induced, for instance by means of a laser which operates in the UV range, in the infrared range, or in the range of visible light and heats up the carrier.

If desired, the decomposition may also be effected by photolysis. Photolytic decomposition may be brought about by means of a laser operated at the appropriate wavelength or by means of a UV lamp.

The decomposition may also be plasma-induced, for instance, by low-pressure plasma, for instance a D.C. or A.C. plasma (low-frequency, medium-frequency, or high-frequency microwave plasma) or glow discharge plasma. The plasma-induced decomposition may be carried out in known plasma reactors, for instance, tubular, tunnel, parallelplate or corona discharge reactors. The decomposition in plasma is usually carried out at reduced pressure, for instance below 10 mbar, .e.g. between $10^{-2}$ and 1 mbar. In this manner, for instance, substrates having relatively low thermostability, such as plastics, may also be coated.

The form in which the alkaline earth metal is present in the layer can be influenced by adding a reactive gas. This, and the possibility of simultaneous or successive deposition of other metals will be described hereinafter.

Another embodiment of the process according to the invention for depositing layers containing alkaline earth metal involves decomposing the starting compound in the gas or vapor phase. The compounds according to the invention are particularly well suited for this embodiment due to their uniform evaporation. Deposition from the gas or vapor phase (in addition to the starting compound which is present in gas form, the vapor phase contains extremely finely distributed portions of the starting compound which is present in condensed form) enables deposition of especially adherent, uniform, thin layers.

The pressure in the vapor phase or gas phase may be more or less high. For instance, it is possible to operate at a pressure which corresponds to the vapor pressure of the starting compound used at the operating temperature. However, the total pressure may also be higher, up to standard pressure. It is preferred to operate at reduced pressure, for instance at $10^{-2}$ to 10 mbar, particularly preferably at 0.1 to 1 mbar.

The starting compound is advantageously decomposed in the vapor phase or gas phase by a metal organic chemical vapor deposition (MOCVD) process.

The principle of the method for coating substrates using the MOCVD process and also suitable apparatus for this purpose are known. Published European Patent Application No. EP 297,348 (which relates to different coatings) gives a person skilled in the art detailed information on how such a process is to be performed and what apparatus can be used.

The decomposition from the gas phase or vapor phase is advantageously performed in a pressure-tight apparatus which can be evacuated. The substrate which is to be coated is introduced into this apparatus. At reduced pressure, an atmosphere is produced which contains the starting compound of the general formula (I) containing alkaline earth metal. In addition to the gaseous or vaporous starting compound, inert gas or reactive gas may be present in the gas space of the apparatus, if desired.

In one variant, the starting compound is introduced in solid form into the apparatus together with the substrate which is to be coated, and not transformed into the gas or vapor phase until it is in the apparatus.

In another, preferred variant, initially only the substrate is introduced into the pressure-tight apparatus, and the starting compound, which is already in gaseous or vaporous form, is continuously or intermittently introduced into the apparatus via a special line. Here too, a carrier gas may be used.

The transformation of the starting compound into the gas or vapor phase can be promoted by heating and if desired by adding a carrier gas.

The decomposition may be effected by known methods. It is possible to bring about the decomposition thermally, by the action of a plasma and/or photolytically.

The thermal decomposition from the gas or vapor phase is usually performed so that the walls of the apparatus are kept cold and the substrate is heated to a temperature at which the desired layer is deposited on the substrate. Persons skilled in the art can readily determine the minimum temperature required for the compound used in each case by simple orientating tests. Usually, the temperature to which the substrate is heated is above about 80° C. For example, the temperature for decomposition of Ba(TMHD)$_2$ according to the invention is above 200° C.

The substrates may be heated in conventional manner, for instance by resistance heating, inductive heating, electric heating apparatus such as heating coils, or the like. The substrates may also be heated by radiation energy. Laser radiation energy is particularly suitable for this. For instance, lasers may be used which operate in the band of visible light, in the ultraviolet (UV) range or in the infrared (IR) range. Lasers have the advantage that they can be focussed to a greater or lesser extent and can therefore specifically heat certain limited areas or points on the substrate.

Since the thermal CVD process is usually carried out at low pressure, it will be apparent to a person skilled in the art to provide pressure-tight apparatus such as are used in high-vacuum techniques. The apparatus advantageously will comprise gas lines which can be heated for the organometallic compound used or the inert gas, openings which can be blocked for letting gas in and out, optional openings for supplying a carrier or reactive gas, temperature measuring means, if desired an opening for supplying the organometallic compound used, a means for heating the substrate, a pump suitable for producing the desired underpressure, etc. If a CVD process induced by radiation energy is to be performed, a radiation source must also be present which emits radiation in the band of visible light, the infrared range or ultraviolet range. Appropriate laser radiation energy sources are particularly suitable. The substrate can be heated by means of the radiation energy.

Figure 1:
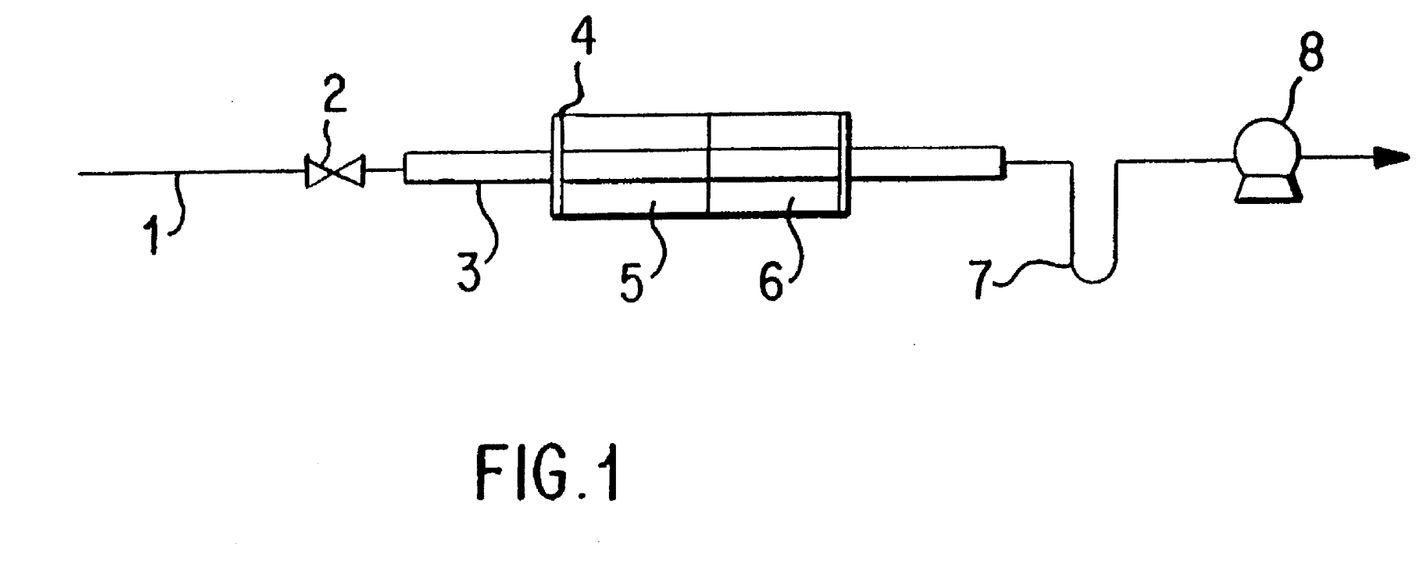
FIG. 1 is a schematic illustration of an apparatus adapted to form alkaline earth metal-containing layers by decomposing a compound in accordance with the invention.

A very simple, advantageous apparatus for performing the process is shown schematically in FIG. 1. It comprises a glass tube 3 connected to an inert gas inlet line 1 via a valve 2 which can be shut off. Glass tube 3 is arranged concentrically in a tubular heating furnace 4 which has two heating zones 5 and 6 ("two-zone tube furnace"). The other side of the tube is connected via a freezing trap 7 to a vacuum pump 8.

In operation, the starting compound is introduced into the first heating zone, which is located on the side of the inert gas inlet line. The substrate is introduced into the second heating zone, which is located on the side of the vacuum pump.

As already stated, the decomposition may also be brought about photolytically. For instance, the decomposition may be brought about by plasma-inducement. As already described above, for instance a D.C. plasma, high-frequency plasma, microwave plasma or glow discharge plasma is used. Furthermore, photolytic decomposition may be effected by using a laser operating at a suitable wavelength.

Without giving an explanation of the formation of layers by the decomposition of the alkaline earth metal compounds, it is assumed that gases or vapors of the compound reach the heated substrate and are decomposed thereon, forming the layers containing alkaline earth metal. The thickness of the layers depends essentially on the length of the deposition, on the partial pressure in the gas space, and on the deposition temperature. Thicker or thinner layers can be produced, for instance layers having a thickness of up to 20 micrometers, for instance between 100 Å and 20 micrometers. Depending on the desired layer thickness, persons skilled in the art can readily determine the time and deposition temperature required to produce a layer of a given thickness by simple tests.

As already stated, the decomposition may also be brought about photolytically, for instance by a UV lamp or by a laser operating at a suitable wavelength.

The gas space surrounding the substrate contains the starting compound which is present in gaseous or vaporous form. It has already been mentioned earlier that an inert gas or a reactive gas may also be contained in the gas atmosphere. Depending on the manner of deposition, layers containing alkaline earth metal are deposited which contain the alkaline earth metal in metallic form or alternatively in the form of certain chemical compounds.

If the starting compound is decomposed without the addition of a reactive gas, alkaline earth metal-containing layers are deposited which contain the alkaline earth metal essentially in the form of the oxide.

The substrates coated according to the invention may be subjected to subsequent treatment. To produce layers which contain the alkaline earth metal in metallic form, a reducing atmosphere may be allowed to act on the layer. Substrates coated in this way may be used, for instance, as getters.

One possible subsequent treatment provides for the layers to be exposed to a hydrolyzing atmosphere. With water, first of all a layer which contains an alkaline earth metal hydroxide is formed. Alkaline earth metal hydroxides are known likewise to be very reactive, and may for instance be converted with carbon dioxide into the alkaline earth metal carbonate. Alkaline earth metal carbonates, on the other hand, and also alkaline earth metal hydroxides, maybe converted into the corresponding alkaline earth metal oxides by calcination. In this manner, it is possible to produce substrates coated with alkaline earth metal hydroxide, alkaline earth metal carbonate or alkaline earth metal oxide. Substrates coated in this way may be used, for instance, as optical layers.

In another embodiment, the decomposition is carried out in a reactive gas atmosphere, in particular in an oxidizing atmosphere. This variant will be described further with reference to the preferred embodiment of the process according to the invention for depositing layers containing alkaline earth metal, namely decomposition in an oxidizing gas atmosphere. Advantageously, the decomposition is carried out in the presence of an oxidizing gas atmosphere, for instance one containing oxygen, nitrogen dioxide or ozone. Layers containing alkaline earth metal are then formed which contain the alkaline earth metal in the form of alkaline earth metal oxide.

Alternatively, it is also possible to operate in a hydrolyzing or carbonizing atmosphere, for instance in the presence of water and/or carbon dioxide. The alkaline earth metal carbonate or hydroxide which is produced as an intermediate stage can be subsequently calcined to form the metal oxide. However, it is simpler to carry out the decomposition in the presence of an oxidizing atmosphere, particularly an oxygen-containing atmosphere.

Following the deposition in the oxidizing reactive gas atmosphere, if desired, the deposited layers may be subjected to subsequent treatment, in particular to oxidizing subsequent treatment.

The process according to the invention is also suitable for depositing layers which contain one or more other metals in addition to the alkaline earth metal. This embodiment of the deposition process according to the invention is characterized in that for depositing layers containing alkaline earth metal and which furthermore contain one or more other metals, one or more compounds of other metals and a compound of the general formula (I) are decomposed simultaneously or successively.

If the deposition is performed from the condensed phase, mixtures are used which in addition to a starting compound of the general formula (I) contain any known decomposable compounds desired. Particularly preferably, decomposition is carried out with the formation of layers which contain the alkaline earth metal and the additional metal or metals in the form of the metal oxides. For this purpose, one can operate in a reactive gas atmosphere, as described above, and if desired, the coated substrates may be subjected to a subsequent oxidizing treatment. For instance, decomposable titanium compounds such as titanium alcoholates or titanium-β-diketonates may be used and layers containing alkaline earth metal titanates, in particular barium titanate, may be deposited. Of course, it is also possible to prepare modified alkaline earth metal titanates. For instance, part of the barium may be replaced by lead, calcium or strontium, and/or part of the titanium by tin, zirconium or hafnium. Under such circumstances it is advantageous to start with β-diketonates of these compounds. When depositing from the condensed phase, one can operate in the manner of the known sol-gel process.

The titanates produced in this manner have dielectric properties, and substrates coated with these dielectrics may be used in the electrical engineering and sensor industry.

Furthermore, the compounds of Formula (I) according to the invention are also suitable for use in a deposition process according to the invention, performed from the condensed phase, for producing oxide mixtures containing alkaline earth metal which correspond in their chemical composition to known high-temperature superconducting ceramics, for instance rare earth metal/alkaline earth metal/copper oxide type superconducting ceramics. For example, β-diketonates of yttrium and copper and a barium compound of the general formula (I) may be mixed, decomposed, optionally subsequently treated with oxygen and optionally tempered. A yttrium-barium-copper oxide is then obtained.

If desired, modified mixtures may also be produced by replacing part of the yttrium, barium and/or copper compounds by decomposable compounds of other metals, for instance by calcium compounds according to the invention or known calcium compounds, by strontiumcompounds according to the invention or known strontium compounds, by lanthanum compounds, bismuth compounds, thallium compounds or by other rare earth metal compounds. The desired molar ratio of the metals can be fixed in a simple manner during mixing.

The compounds of the general formula (I) according to the invention are particularly well suited for deposition in the gas or vapor phase because they have a very uniformrate of evaporation.

The compounds of Formula (I) according to the invention are particularly well suited for the production of layers which correspond in their chemical composition to oxide-ceramic high-temperature superconductors, in particular those of the rare earth metal/alkaline earth metal/copper oxide type. Particularly thin, adherent, uniform layers can be produced from the gas or vapor phase.

Carriers conventionally used in CVD processes may be used as carriers. For depositing superconducting layers, it is possible to use as carriers, for instance, strontium titanate, aluminium oxide, magnesium oxide or other materials which are known to be useful carriers or supports. These substrates may, for instance, be in the form of fibers (e.g. carbon fibers), strips, sheets, tubes, or plates.

In order to deposit oxide-ceramic high-temperature superconductors, for instance those of the rare earth metal/alkaline earth metal/copper oxide type, such as $Y_1Ba_2Cu_3O_x$, wherein x is about 6.8 to 6.95, the various metal layers advantageously are deposited in succession. The deposition of the alkaline earth metal in this case takes place according to the process of the invention.

Advantageously, a copper-containing layer initially is deposited by vaporizing a knownvaporizable copper compound, for instance copper acetyl acetonate, copper TMHD or cyclopentadienyl-copper-trialkylphosphine complexes, at reduced pressure and at a temperature between room temperature and about 300° C. or higher and then depositing the vaporized compound on the carrier from an oxidizing gas atmosphere.

The copper compounds of the general formula RO-Cu-L (II), which are known from German published Patent Application No. DE 41 22 449, are also highly suitable for depositing copper-containing layers. R represents in particular branched alkyl with 3 to 6 carbon atoms, L represents t-butyl isonitrile, carbon monoxide and certain trivalent phosphorus compounds. Compounds of this type can be readily prepared by initially reacting the appropriate lithium alcoholate with copper (I) chloride to form the intermediate product RO-Cu, and then allowing the intermediate to react further with the ligand L to form the desired compound of the general formula (II). In particular, the known compounds t-butoxy-copper-t-butyldifluorophosphane, t-butoxy-copper-phenyldifluorophosphane, t-butoxy-copper-diethylaminodifluorophosphane, 2-trifluoromethylpropane-2-oxy-copper-t-butylisonitrile, 2-trifluoromethylpropane-2-oxy-copper-trimethylphosphane, perfluoro-t-butoxy-copper-t- butylisonitrile, and perfluoro-t-butoxy-copper-trimethylphosphane are highly suitable.

The compounds of the general formula R-Cu-L (III), which are described as usable in German published Patent Application No. DE 41 24 686, are also highly suitable. In this case R represents cyclopentadienyl or cyclopentadienyl substituted by 1 to 5 substituents, in particular alkyl having 1 to 5 carbon atoms. L represents ($C_1$-$C_6$-alkyl)isonitrile or arylisonitrile, Compounds of this type can be produced by reacting anhydrous copper (I) chloride with t-BuO-Li to form t-BuO-Cu, and reacting this product with an isonitrile, for instance t-BuNC to form t-BuO-Cu-t-BuNC. This intermediate compound is then converted into the desired compound of the general formula (III) by reaction with a cyclopentadiene or a substituted cyclopentadiene. For instance, $C_5H_5$-Cu-t-BuNC is very highly suitable. After deposition of the copper-containing layer, the layer containing rare earth metal advantageously is deposited. For instance, compounds of yttrium, in particular β-diketonates are vaporized, such as yttrium-tris(2,2,6,6-tetramethyl-3,5-heptane dionate). After the decomposition of these compounds, a compound of the general formula (I) according to the invention, for instance, barium-bis-2,2,6,6-tetramethyl-3,5-heptane dione, is vaporized and decomposed in order to deposit the layer containing alkaline earth metal. The decomposition temperature is about 500° C. to 700° C.

If desired, the sequence of deposition of layers described above may also be varied. The coating may then be tempered to convert the deposited oxide layer into a high-temperature superconductor.

It is possible to produce modified oxide-ceramic layers in a completely analogous manner by replacing all or part of the yttrium with strontium, lanthanum, thallium, bismuth or other metals. Additionally or instead of this, all or part of the barium may be replaced by other alkaline earth metals. Advantageously, metal-β-diketonates are used. For depositing layers containing alkaline earth metal which in addition to barium or instead of barium contain other alkaline earth metals, the compounds of the general formula (I) according to the invention in which M is calcium or strontium are used.

In this manner, it is possible also to produce superconductors based on thallium oxide or bismuth oxide in addition to optionally modified superconductors of the rare earth metal-alkaline earth metal-cuprate type.

Apart from the method described above for producing high-temperature superconductors by successive deposition of layers, of course it is also possible to start with mixtures and then deposit homogenous layers.

Furthermore, apart from the deposition from the gas or vapor phase as described above, it is also possible to deposit from the condensed phase, as described further above.

The thickness of the deposited superconductive layer is advantageously about 5 to 20 micrometers.

The following examples are intended to illustrate the invention in greater detail, without restricting its scope.

EXAMPLE 1: Preparation of barium-bis(2,2,6,6-tetramethyl-3,5-heptane dionate) (according to the invention).

22.08 g of barium hydroxide octahydrate (0.07 mole) were suspended in 120 ml of distilled water in a 250 ml round-bottomed flask. 25.8 g (0.14 mole) of 2,2,6,6-tetramethyl-3,5-heptane dione were added in drops to the white suspension. A white solid was formed. The reaction mixture was stirred further for 10 hours at 50° C. oil bath temperature. After cooling to room temperature, the white product was then filtered out with a suction filter. A water-jet vacuum was applied in order to accelerate the filtration. The solid which had been filtered out was then subsequently washed with distilled water and substantially dried by suction in the water-jet vacuum. The moist yield was 40.5 g. The pre-dried product was then dried for 4 hours in an oil pump vacuum at about $10^{-2}$ to $10^{-3}$ Torr with heating on a 50° to 55° C. oil bath. The yield was 33.5 g (95.7% of theoretical).

| Elemental Analysis | Ba [%] |
|---|---|
| calculated: | 27.25 |
| found: | 27.1 |

In the $^1$H-NMR spectrum of a solution of the Ba(TMHD)$_2$ according to the invention in $D_6$-DMSO, no signal for $H_2O$ protons could be identified even at a signal-to-noise ratio of >600.

Roentgen spectrum: 2theta=23.99°; 16.7°; 6.3°; 7.0°; (selected peaks) 7.4°; 5.6°.

Determination of the weight loss at 200° C. in a vacuum:

A NETZSCH simultaneous thermoanalysis apparatus STA 409 was used to determine the weight loss in a vacuum. A sample of 81.00 mg of the Ba(TMHD)$_2$ produced in Example 1 according to the invention was placed in an aluminium oxide crucible and introduced into the thermoanalysis apparatus. Aluminium oxide (56.00 mg) served as a reference. The atmosphere in the apparatus consisted of nitrogen, and the pressure was 10 Torr. After the sample had been introduced, the temperature in the analysis apparatus was increased to 200° C. This temperature was reached after half an hour. The change in weight of the sample over a period of about 460 minutes beginning with the introduction of the sample into the thermoanalysis apparatus was plotted by a recorder. The results are shown as a graph in FIG. 2. The duration of the test in minutes (min.) from time 0 ($t_0$=time of introduction of the sample into the analysis apparatus) to the discontinuance of the test after about 470 minutes is plotted on the abscissa. The loss in weight during the test is plotted on the left ordinate in the form of negative percentages, each relative to the total weight of the original sample. The right ordinate gives the temperature. The original weight of the sample introduced into the analysis apparatus is arbitrarily set at 0. A sample having a weight loss of "−10%" will then correspond to a sample which still has 90% of its original weight. The associated curve which gives the weight loss over the duration of the test is marked "TG" in FIG. 2. The curve which gives the temperature gradient during the test is marked "Temp" in FIG. 2.

Figure 2:
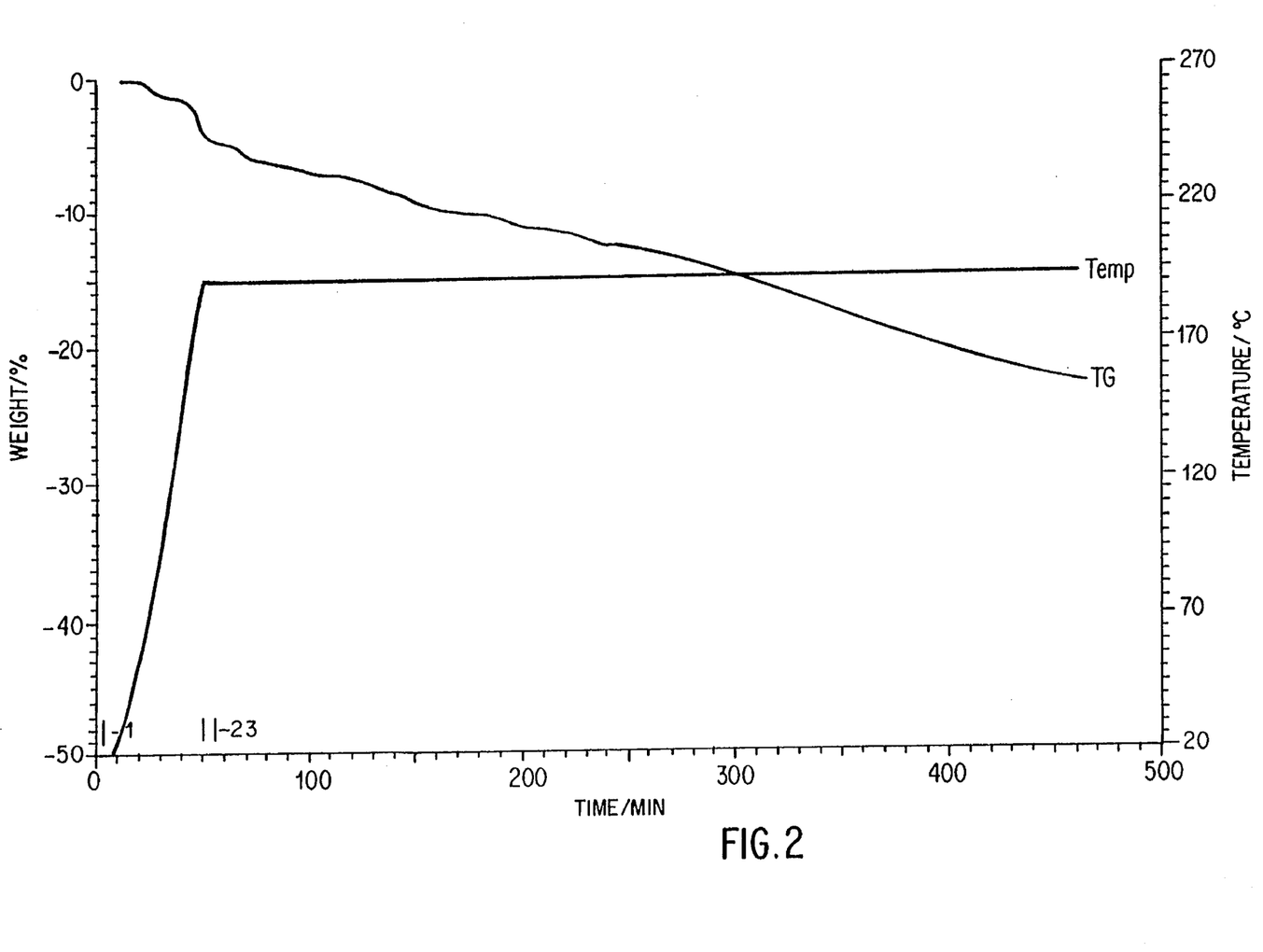
FIG. 2 is a graph showing the weight loss over time of heated sample of $Ba(TMHD)_2$ produced according to the invention.

Table 1 lists values, obtainable from FIG. 2, for the weight loss of the sample and the corresponding residual weights of the sample calculated therefrom, at certain measuring times $t_0$, $t_1$, etc.

TABLE 1

| | Measurement Time (min.) | Sample Weight Loss (% by wt.) | Calc. Residual Sample Weight (% by wt.) |
|---|---|---|---|
| $t_0$* | 0 | 0 | 100 |
| $t_1$** | 50 | −3.5 | 96.5 |
| $t_2$ | 110 | −7 | 93 |
| $t_3$ | 170 | −10 | 90 |
| $t_4$ | 230 | −12.5 | 87.5 |
| $t_5$ | 290 | −15 | 85 |
| $t_6$ | 350 | −18 | 82 |

TABLE 1-continued

| Measurement Time (min.) | Sample Weight Loss (% by wt.) | Calc. Residual Sample Weight (% by wt.) |
|---|---|---|
| $t_7$ 410 | −21.5 | 78.5 |

*$t_0$ = time of start of test
**$t_1$ = time predetermined temperature (200° C.) was attained in the analysis apparatus It can be seen from Table 1 that during a test period of 410 minutes, the weight loss per unit of time lies within a range which fluctuates only slightly. For instance, the average weight loss between the time $t_1$ (time at which the predetermined temperature Was attained in the analysis apparatus) to the time $t_7$ is about −18% by weight. The average weight loss between two successive measuring times is then about −3% by weight, relative to the weight of the sample at the time $t_0$ (start of test). A look at Table 1 will show that the actual weight loss between two successive measuring times fluctuates between −2.5% by weight (difference between the results at the measuring times $t_3$ and $t_4$ or $t_4$ and $t_5$) and −3.5% by weight (weight loss between the measuring times $t_1$ and $t_2$ or $t_6$ and $t_7$). Such a slight range of fluctuation is very advantageous for application in CVD processes.

Determination of the rate of evaporation:

The apparatus used comprised a vessel which could be evacuated, which was connected to a vacuum pump and to a gas feed line through which a carrier gas could be introduced into the vessel. The carrier gas could be heated to a predetermined temperature by a gas preheating means. The vessel was furthermore connected in gas-tight manner to a microbalance, the measuring signals of which acted on a recording apparatus via electronic components and a computer. The temperature of the sample could be monitored and adjusted by means of the gas preheating means and corresponding heating elements.

Figure 3:
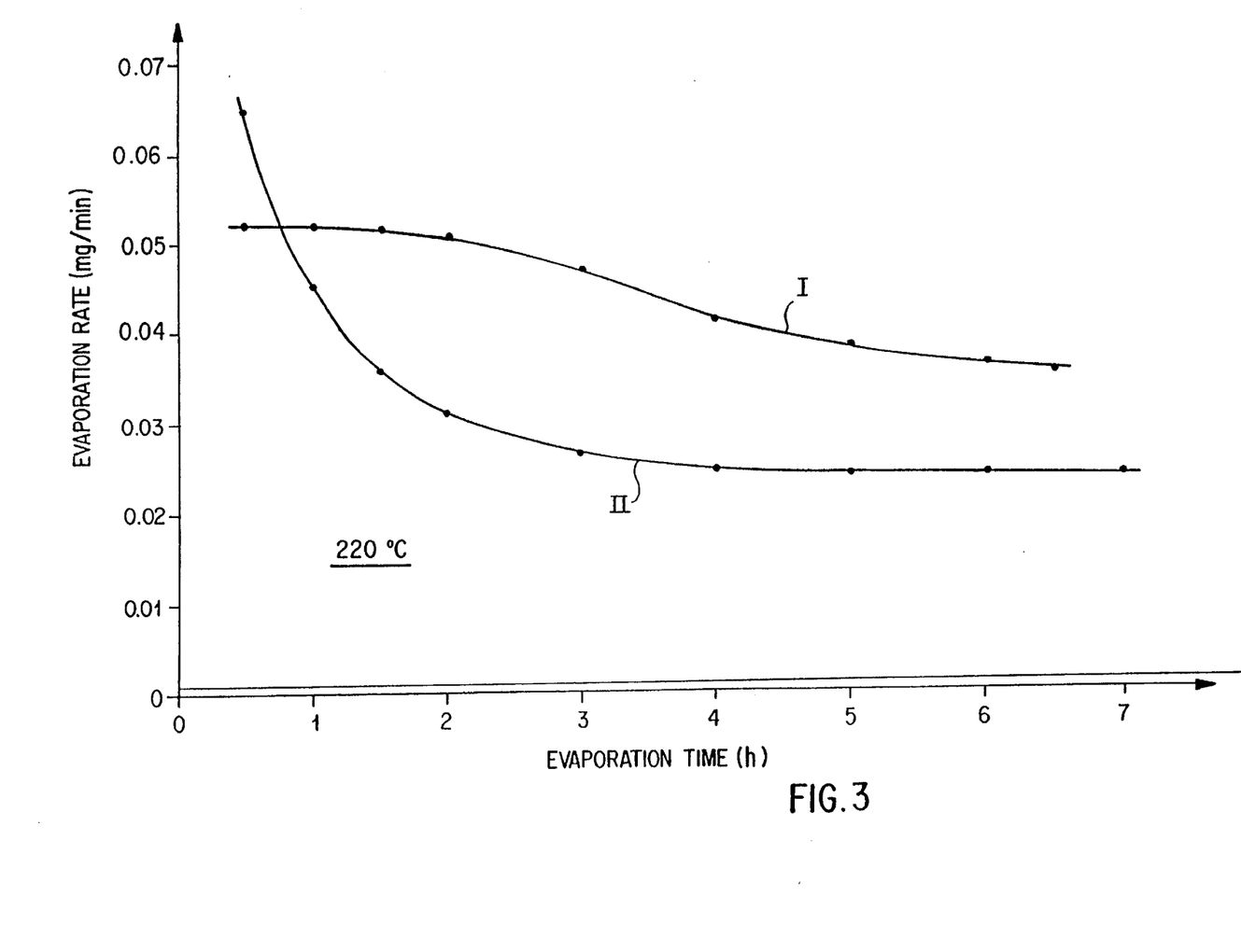
FIG. 3 is a comparative graph showing the evaporation rate over time of heated Samples of $Ba(TMHD)_2$ produced according to the invention and by prior art techniques.

The sample to be measured was introduced in a small crucible into the vessel which could be evacuated, in such a manner that the crucible was freely suspended on a thread which was connected to the microbalance so that weight losses registered on the microbalance. The gas preheating means was regulated so that the test sample had a temperature of 220° C. The vessel was then evacuated with an oil pump (10 mbar vacuum). Changes in weight of the test sample which were registered by the microbalance were converted by the computer into an evaporation rate in mg/min and were plotted by the recorder. FIG. 3, graph I shows the curve of the evaporation rate of a sample of Ba(TMHD)$_2$ prepared according to Example 1 at 220° C. over a period of 6 hours. Table 2 lists numerical values, obtainable from FIG. 3, for the evaporation rate after about 30 minutes and also after 1, 2, 3, 4, 5 and 6 hours.

TABLE 2

| Measurement Time (min.) | Evaporation Rate (mg/min) |
|---|---|
| $t_0$* 0 | — |
| $t_1$ 0.5 | 0.052 |
| $t_2$ 1 | 0.0518 |
| $t_3$ 2 | 0.050 |
| $t_4$ 3 | 0.047 |
| $t_5$ 4 | 0.041 |
| $t_6$ 5 | 0.038 |
| $t_7$ 6 | 0.036 |

*$t_0$ = start of measurement

As can be seen from Table 2, the evaporation rate drops from 0.052 mg/min to 0.036 mg/min between the measuring times $t_1$ and $t_7$. This means that 5½ hours after the start of measuring, the evaporation rate is still 69.2% of the initial value. Furthermore, the evaporation rate decreases uniformly. Due to this rather slight and highly uniform decrease in its evaporation rate, the Ba(TMHD)$_2$ according to the invention is highly suitable for use in CVD synthesis.

EXAMPLE 2 (comparison example): Preparation of Ba(TMHD)$_2$ from anhydrous solvents.

37.8 g of bariumhydroxide octahydrate (0.12 mole) were placed in a 250 ml round-bottomed flask. 50 ml of 2,2,6,6-tetramethyl-3,5-heptane dione (0.24 mole) were added in drops via a dropping funnel. Then 70 ml of xylene were added. The reaction mixture was then heated to 50° C. by means of an oil bath and stirred at this temperature for 10 hours. Then the oil bath temperature was adjusted to 60° C. and volatile constituents were distilled off under high vacuum.

Dry yield: 57.5 g (95% of theoretical).

According to elemental analysis, 1% more barium was contained in the sample than had been calculated. Therefore 100 ml hexane were mixed with the resulting Ba(TMHD)$_2$ and another 8 ml TMHD (7.16 g, corresponding to 0.0384 mole) were added. Then the reaction mixture was stirred at a temperature of 50° C. for a further 8 hours and subsequently dried under high vacuum as described above.

| Elemental Analysis | Ba [%] |
|---|---|
| calculated: | 27.25 |
| found: | 27.4 |

In the $^1$H-NMR spectrum of a solution of the product in D$_6$-DMSO, a signal of water protons can clearly be identified.

Determination of the rate of evaporation:

The apparatus described in Example 1 was used to determine the evaporation rate. The determination was performed analogously to the method described in Example 1. FIG. 3, graph II shows the curve of the evaporation rate. The measured results determined therefrom are listed in Table 3.

TABLE 3

(comparison example 2)

| Measurement Time (hours) | Evaporation Rate (mg/min) |
|---|---|
| $t_0$* 0.5 | 0.065 |
| $t_1$ 1 | 0.045 |
| $t_2$ 2 | 0.031 |
| $t_3$ 3 | 0.027 |
| $t_4$ 4 | 0.0245 |
| $t_5$ 5 | 0.024 |
| $t_6$ 6 | 0.024 |

*$t_0$ = start of measurement

It can be seen from the table that the evaporation rate has decreased from 0.065 mg/min initially to a value of only 0.024 mg/min after 5½ hours. This is only 37% of the initial value. Furthermore, the decrease in the evaporation rate is initially very great. Such a large and irregular decrease is very disadvantageous for most applications.

EXAMPLE 3: Preparation of calcium-bis(2,2,6,6-tetramethyl-3,5-heptane dionate) (according to the invention).

3.7 g of calcium hydroxide (0.05 mole) were suspended in about 100 ml of distilled water in a 250 ml round-bottomed flask. 18.4 g of TMHD (0.1 mole) were added in drops to the resulting white suspension with stirring. A white solid was formed. The reaction mixture was then adjusted to a temperature of 50° C. by means of an oil bath and stirred for 10 hours at this temperature. After cooling to room temperature, the white product was filtered out with a suction filter and was subsequently washed with distilled water. The moist yield after drying to a substantial extent by suction in a water-jet vacuum was 25.0 g. The solid was then heated by means of an oil bath which was maintained at a temperature of 50° C. and dried under a high vacuum (oil pump) at about $10^{-2}$ to $10^{-3}$ Torr.

Dry yield: 18.8 g (94% of theoretical)

Melting behavior:

Immediately after preparation: at 255° C. formation of a cloudy molten mass.

After 30 days: sintering at 245° C., formation of a cloudy molten mass at 250° C.

| Elemental Analysis | Ca [%] |
| --- | --- |
| calculated: | 9.86 |
| found: | 10.2 |

Figure 4:
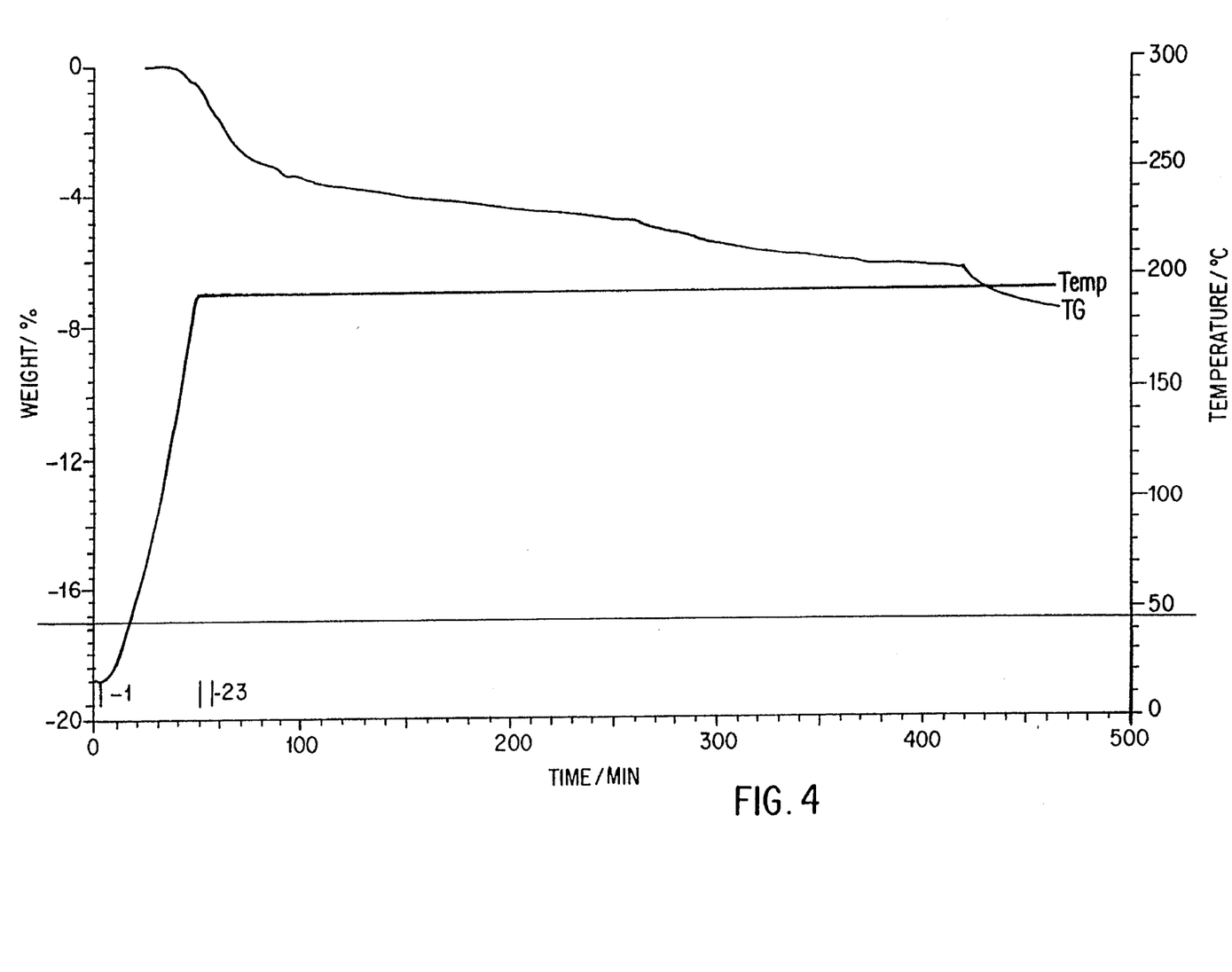
FIG. 4 is a graph showing the weight loss over time of sample of $Ca(TMHD)_2$ according to the invention heated under an air atmosphere.

Determination of the weight loss at 200° C. in a vacuum:

The apparatus produced by Netzsch, also used in Example 1, was again used. The reduction in weight was measured a) under an air atmosphere and b) under a nitrogen atmosphere.

a) Measurement of weight loss under an air atmosphere:

In order to determine the weight loss, a sample of 93.00 mg of the $Ca(TMHD)_2$ according to the invention produced in Example 3 was placed in an aluminium oxide crucible and introduced into the thermoanalysis apparatus. Aluminium oxide (90.00 mg) served as a reference. As noted above, the atmosphere in the apparatus consisted of air, and the pressure was about 10 Torr. Once the sample had been introduced, the temperature in the analysis apparatus was increased to 200° C. within half an hour. The change in weight of the sample was plotted as already described in Example 1 over a period of about 460 minutes by means of a recorder. A graph of the results is shown in FIG. 4. The curve showing the weight loss throughout the duration of the test is again marked "TG" and the curve of the temperature gradient is again marked "Temp".

Table 4 lists values, obtainable from FIG. 4, for the weight loss of the sample and the corresponding residual weights of the sample calculated therefrom at predetermined measurement times $t_0$, $t_1$, etc.

TABLE 4

| | Measurement Time (min.) | Sample Weight Loss (% by wt.) | Calc. Residual Sample Weight (% by wt.) |
| --- | --- | --- | --- |
| $t_0$* | 0 | 0 | 100 |
| $t_1$** | 50 | −0.77 | 99.23 |
| $t_a$ | 80 | −3 | 97 |
| $t_2$ | 110 | −3.7 | 96.3 |
| $t_3$ | 170 | −4.3 | 95.7 |
| $t_4$ | 230 | −4.8 | 95.2 |
| $t_5$ | 290 | −5.5 | 94.5 |
| $t_6$ | 350 | −6.1 | 93.9 |
| $t_7$ | 410 | −6.5 | 93.5 |

Figure 5:
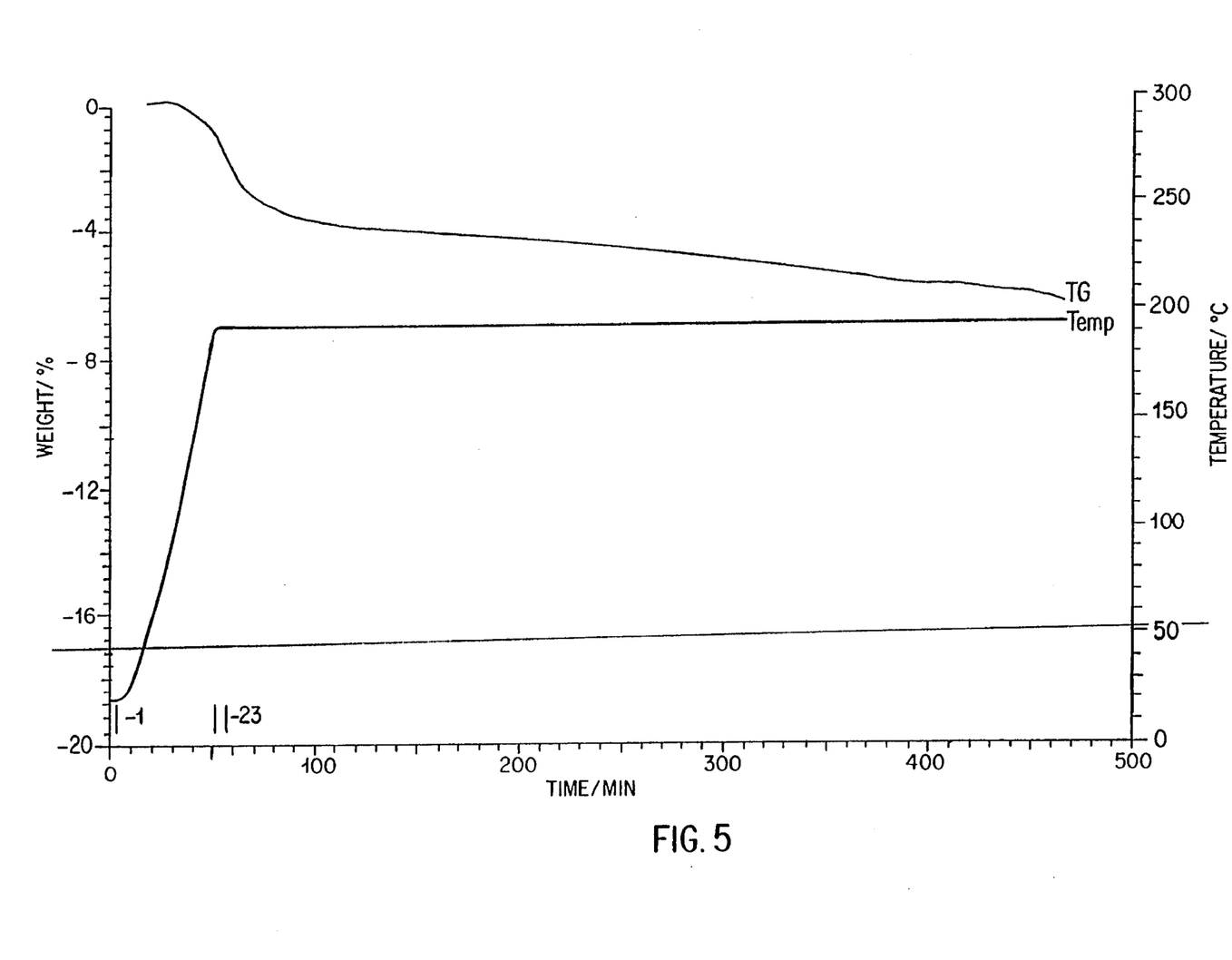
FIG. 5 is a graph showing the weight loss over time of sample of $Ca(TMHD)_2$ according to the invention heated under a nitrogen atmosphere.

*$t_0$ = time of start of test
**$t_1$ = time predetermined temperature (200° C.) was attained in the analysis apparatus It can be seen from Table 4 that as soon as 30 minutes ($t_a$) after the predetermined temperature of 200° C. has been reached, the weight loss per unit of time is very uniform in the following 330 minutes. The absolute amount of weight loss per hour is in the range of (0.56±0.16) % by weight. Due to this slight range of fluctuation, the $Ca(TMHD)_2$ according to the invention can be used very advantageously in CVD processes.

b) Measurement of weight loss under a nitrogen atmosphere:

In this test, a sample of 83.00 mg of the $Ca(TMHD)_2$ according to the invention produced in Example 3 was placed in an aluminium oxide crucible and introduced into the thermoanalysis apparatus. Aluminium oxide (89.00 mg) served as a reference. The atmosphere in the apparatus consisted of nitrogen, and the pressure was about 10 Torr. Once the sample had been introduced, the temperature in the analysis apparatus was increased to about 200° C. within half an hour. The change in weight of the sample was plotted by means of a recorder over a period of about 460 minutes, beginning with the introduction of the sample into the thermoanalysis apparatus. A graph of the results is shown in FIG. 5. The curve showing the weight loss throughout the duration of the test is again marked "TG" and the curve of the temperature gradient is again marked "Temp" in FIG. 5.

Table 5 lists values, obtainable from FIG. 5, for the weight loss of the sample and the corresponding residual weights of the sample calculated therefrom at certain measuring times $t_0$, $t_1$, etc.

TABLE 5

| | Measurement Time (min.) | Sample Weight Loss (% by wt.) | Calc. Residual Sample Weight (% by wt.) |
| --- | --- | --- | --- |
| $t_0$* | 0 | 0 | 100 |
| $t_1$** | 50 | −1.1 | 98.9 |
| $t_a$ | 80 | −3.3 | 96.7 |
| $t_2$ | 110 | −3.9 | 96.1 |
| $t_3$ | 170 | −4.2 | 95.8 |
| $t_4$ | 230 | −4.45 | 95.55 |
| $t_5$ | 290 | −4.9 | 95.1 |
| $t_6$ | 350 | −5.3 | 94.7 |
| $t_7$ | 410 | −5.8 | 94.2 |

*$t_0$ = time of start of test
**$t_1$ = time predetermined temperature (200° C.) was attained in the analysis apparatus It can be seen from Table 5 that the weight loss under the nitrogen atmosphere per unit of time also fluctuates only slightly over the course of several hours. Although a larger than average decrease in weight was observed during the first 30 minutes after the predetermined temperature of 200° C. was reached, about 1 hour after the predetermined temperature was reached the sample vaporizes very uniformly. The absolute value of weight loss is in the range of about (0.38±0.17) % by weight per hour. Thus it is also very advantageous to use the compounds of the invention in a CVD process under a nitrogen atmosphere as well.

EXAMPLE 4: Preparation of Strontium-bis (2,2,6,6-tetramethyl-3,5-heptanedionate).

11.69 g of strontium hydroxide octahydrate (0.044 mole) were suspended in about 100 ml of distilled water in a 250 ml round-bottomed flask. 16.22 g TMHD (0.088 mole) were then added in drops with stirring. A solid was produced. This solid was comminuted with a spatula, and the reaction mixture was then stirred further for 10 hours with heating with an oil bath maintained at a temperature of 50° C. The solid was then filtered out with a suction filter, washed with distilled water, and pre-dried with a water-jet pump. The moist yield was 24.2 g. The solid was then dried in an oil pump vacuum at about $10^{-2}$ to $10^{-3}$ Torr with heating on an oil bath maintained at a temperature of 50° C.

Yield: 18.7 g (93.5% of theoretical).

| Elemental Analysis | Sr [%] |
|---|---|
| calculated: | 19.29 |
| found: | 20.1 |

Melting behavior:

immediately after preparation: sintering at 140° C., formation of a whitish, cloudy molten mass at 250° C.

after 30 days: sintering at 145° C., formation of a whitish-yellow, cloudy molten mass at 240° C.

EXAMPLE 5: Use of Ba(TMHD)$_2$ to produce barium-containing layers.

Gaseous Cu(TMHD)$_2$ was initially introduced into a CVD apparatus and decomposed on a strontium titanate carrier, forming a layer containing copper essentially as an oxide. Then Y(TMHD)$_3$ was decomposed thermally, forming a layer containing yttrium essentially as an oxide. Finally, Ba(TMHD)$_2$ according to the invention, prepared in accordance with Example 1, was vaporized and introduced into the CVD apparatus. Upon decomposition, a layer which contained barium essentially in the form of its oxide was deposited on the carrier which had been heated to 600° C. Subsequently, the deposited multi-layer omposite was tempered in an oxygen-containing atmosphere.

The foregoing description and examples have been set forth merely to illustrate the invention and are not intended to be limiting. Since modifications of the described embodiments incorporating the spirit and substance of the invention may occur to persons skilled in the art, the scope of the invention should be construed to include all variations falling within the ambit of the appended claims and equivalents thereof.

What is claimed is:

1. A vaporizable compound corresponding to the formula (I)

$$M(R)_2 \qquad (I)$$

wherein

M represents calcium, strontium or barium, and

R represents 2,6-dimethyl-3,5-heptane dionate, 2,2,6-trimethyl-3,5-heptane dionate, or 2,2,6,6-tetramethyl-3,5-heptane dionate;

said compound exhibiting a $^1$H-NMR spectrum free of a detectable water proton signal.

2. A compound according to claim 1, wherein R is 2,2,6,6-tetramethyl-3,5-heptane dionate.

3. A compound according to claim 1, wherein M is barium.

4. A composition of matter for use in a metal organic chemical vapor deposition process, said composition comprising in admixture at least one vaporizable compound corresponding to the formula (I) and at least one vaporizable organic compound of another metal.

5. A composition of matter according to claim 4, comprising at least one vaporizable compound corresponding to the formula (I) and at least one vaporizable organic compound of yttrium and copper.

6. A process for preparing a compound corresponding to the formula (I):

$$M(R)_2 \qquad (I)$$

wherein

M represents the metal calcium, strontium or barium, and

R represents 2,6-dimethyl-3,5-heptane dionate, 2,2,6-trimethyl-3,5-heptane dionate or 2,2,6,6-tetramethyl-3,5-heptane dionate, said process comprising the steps of:

mixing a solution or suspension of a compound of the metal M in water or in a water-containing water-miscible solvent with a diketone selected from the group consisting of 2,6-dimethyl-3,5-heptane dione, 2,2,6-trimethyl-3,5-heptane dione and 2,2,6,6-tetramethyl-3,5-heptane dione to react said compound of the metal M with said diketone;

separating the resulting compound of Formula (I) from the mixture; and vacuum drying said separated compound of Formula (I) at a temperature of at most 60° C. until said compound of Formula (I) exhibits a $^1$H-NMR spectrum in which a water proton signal cannot be detected.

7. A process according to claim 6, wherein said compound of the metal M is a hydroxide or an oxide of said metal M.

8. A process according to claim 6, wherein said compound of the metal M and said diketone are used in a molar ratio of 1:2 to 1:2.05.

* * * * *